United States Patent
Diomede

(10) Patent No.: US 9,301,901 B1
(45) Date of Patent: Apr. 5, 2016

(54) ORALLY ADMINISTERING A FLAVORED MEDICATION

(71) Applicant: Anthony J. Diomede, River Vale, NJ (US)

(72) Inventor: Anthony J. Diomede, River Vale, NJ (US)

(*) Notice: Subject to any disclaimer, the term of this patent is extended or adjusted under 35 U.S.C. 154(b) by 639 days.

(21) Appl. No.: 13/622,537

(22) Filed: Sep. 19, 2012

Related U.S. Application Data

(63) Continuation-in-part of application No. 12/722,830, filed on Mar. 12, 2010, now Pat. No. 8,292,844.

(51) Int. Cl.
*A61K 9/00* (2006.01)
*A61J 7/00* (2006.01)
*A47G 21/18* (2006.01)

(52) U.S. Cl.
CPC .............. *A61J 7/0053* (2013.01); *A47G 21/183* (2013.01); *A61J 17/006* (2015.05); *A61K 9/0056* (2013.01)

(58) Field of Classification Search
CPC ... A61J 7/0053; A61J 17/006; A61J 11/0005; A23G 3/563; A23G 3/50; A23G 3/56; A47G 21/183; A61K 9/0056
See application file for complete search history.

(56) References Cited

U.S. PATENT DOCUMENTS

| | | | |
|---|---|---|---|
| 2,121,185 A | 6/1938 | Claff | |
| 3,426,755 A | 2/1969 | Clegg | |
| 3,545,980 A | 12/1970 | Stanger | |
| 3,730,737 A * | 5/1973 | Harvey et al. | 426/115 |
| 4,821,895 A | 4/1989 | Roskilly | |
| RE35,577 E | 8/1997 | Coleman | |
| 5,824,012 A * | 10/1998 | Burchett et al. | 606/236 |
| 5,879,699 A | 3/1999 | Lerner | |
| 6,071,261 A | 6/2000 | Augusto | |
| 6,165,495 A | 12/2000 | Blankenship | |
| 6,454,788 B1 | 9/2002 | Ashton | |
| 6,565,899 B1 | 5/2003 | Cecere | |
| 6,730,339 B2 | 5/2004 | Chan | |
| D491,336 S | 6/2004 | Cecere | |
| 2007/0262041 A1 | 11/2007 | Smith | |

OTHER PUBLICATIONS

CRS Technologies, Inc., WinchMaster, Advertising Literature, published prior to Jan. 2001.

* cited by examiner

*Primary Examiner* — Bhisma Mehta
*Assistant Examiner* — Bradley Osinski
(74) *Attorney, Agent, or Firm* — Arthur Jacob

(57) ABSTRACT

An apparatus and method are disclosed for orally administering to a recipient a medication, in a liquid form, and a flavor for rendering the medication more palatable to the recipient. A manually-operated liquid dispenser dispenses a measured dose of the medication at an administering head comprised of an edible flavored material placed within a recipient's mouth. A handle is coupled with the dispenser, by inserting either one into a receptacle of the other, and the dispenser is operated manually to dispense the medication through a dispensing outlet located relative to the administering head to assure administering substantially all of the measured dose of medication to the recipient's mouth while flavor is derived from the edible flavored material for being present with the measured dose of medication.

9 Claims, 10 Drawing Sheets

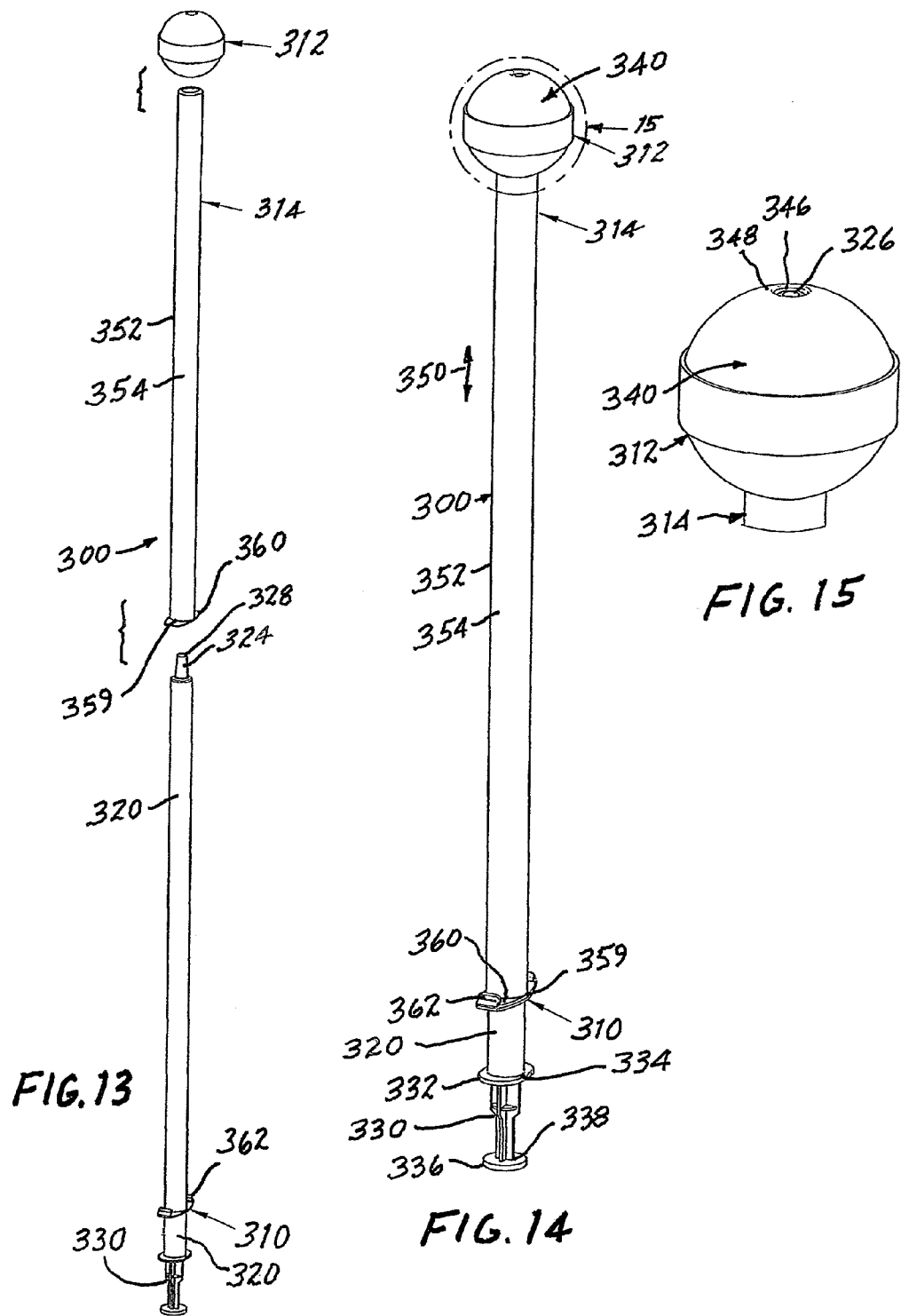

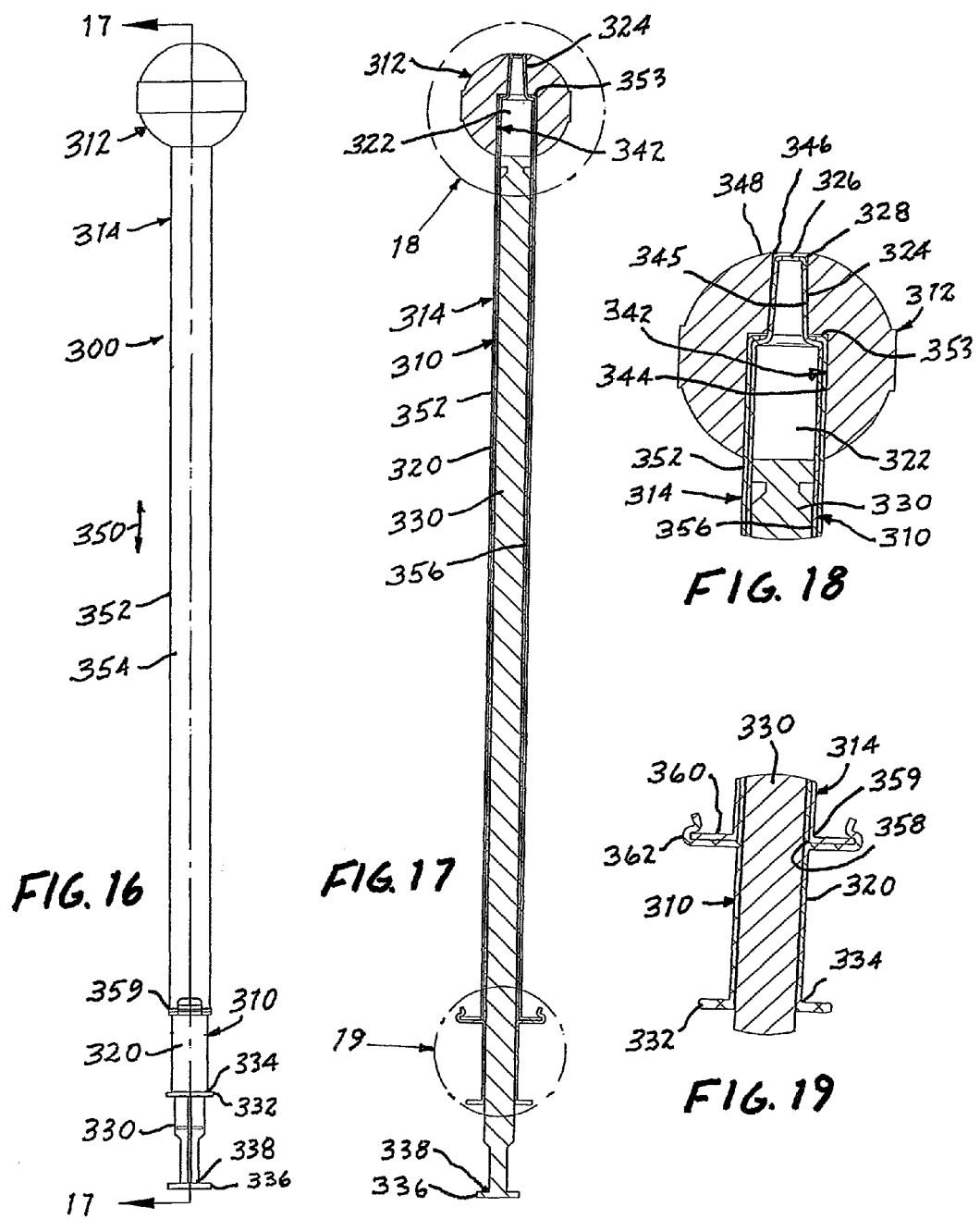

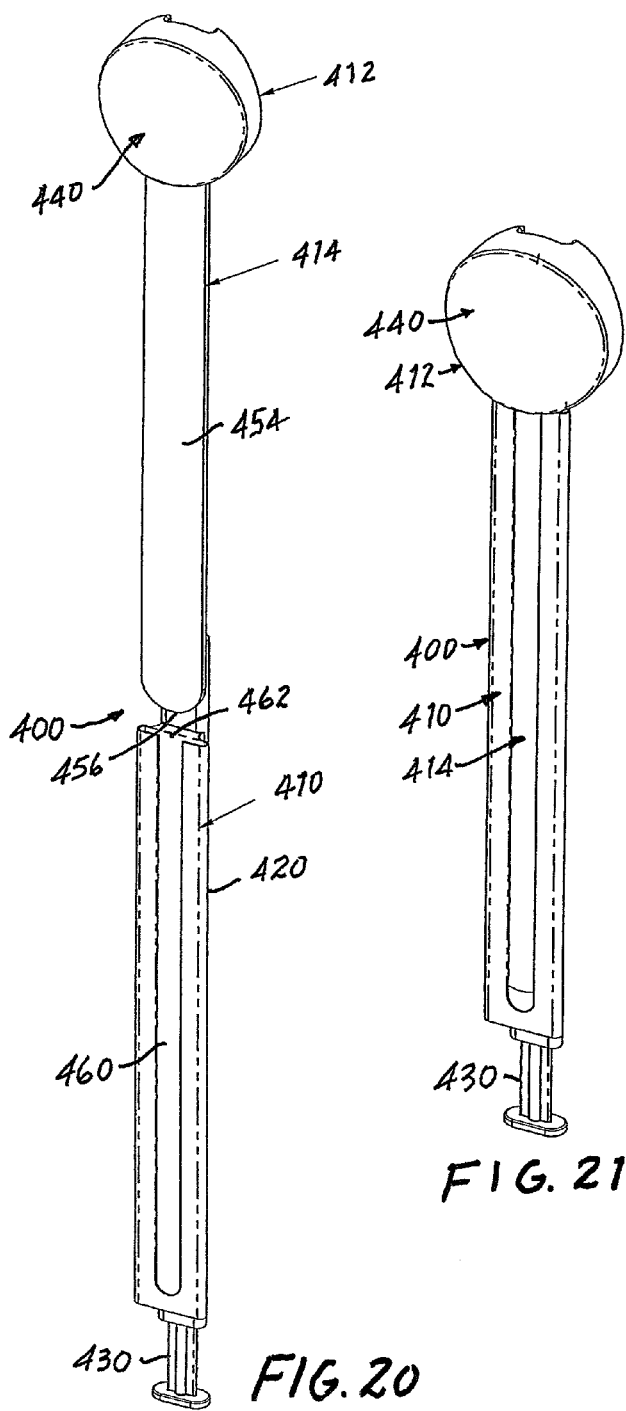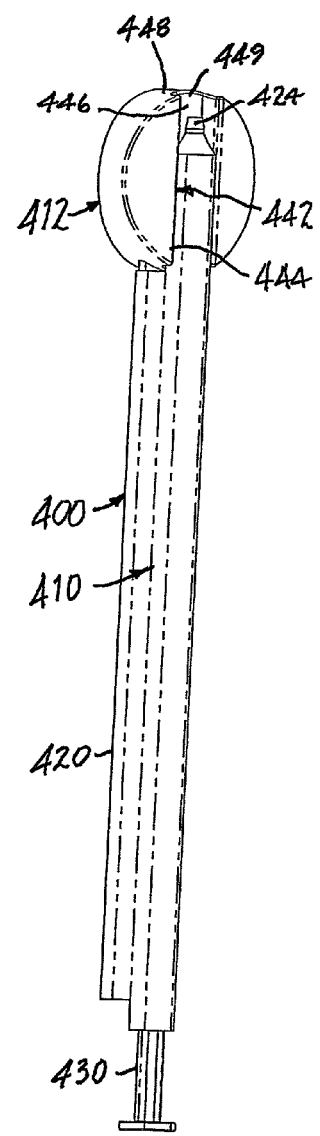
FIG. 20
FIG. 21
FIG. 22

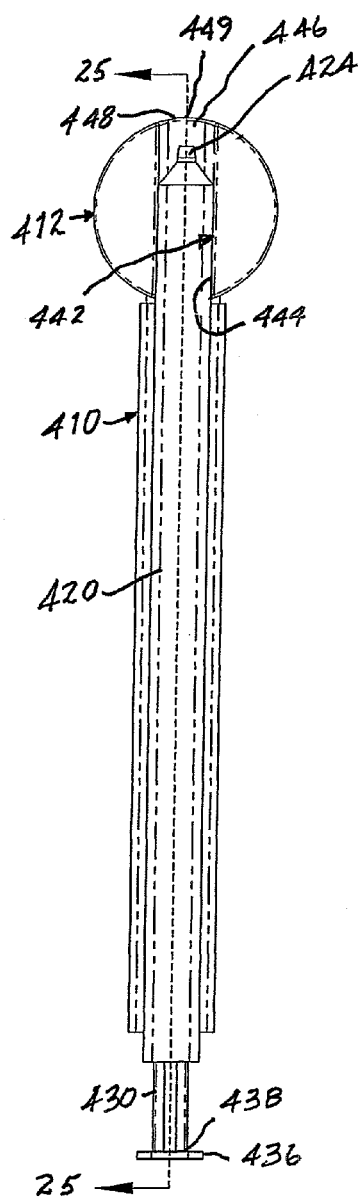
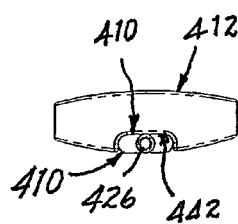
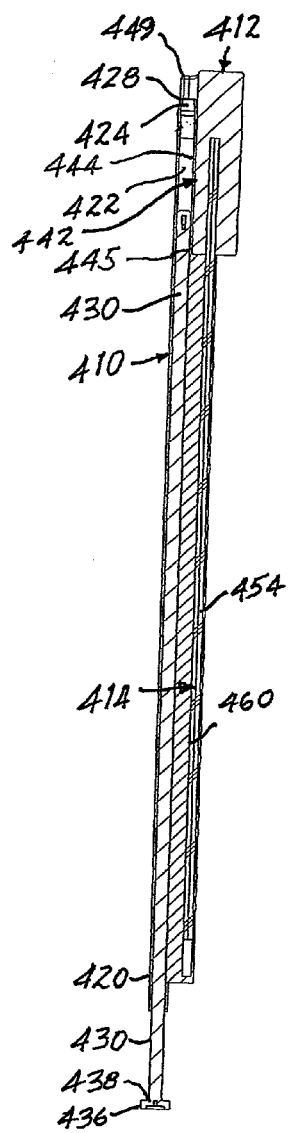
FIG. 23
FIG. 24
FIG. 25

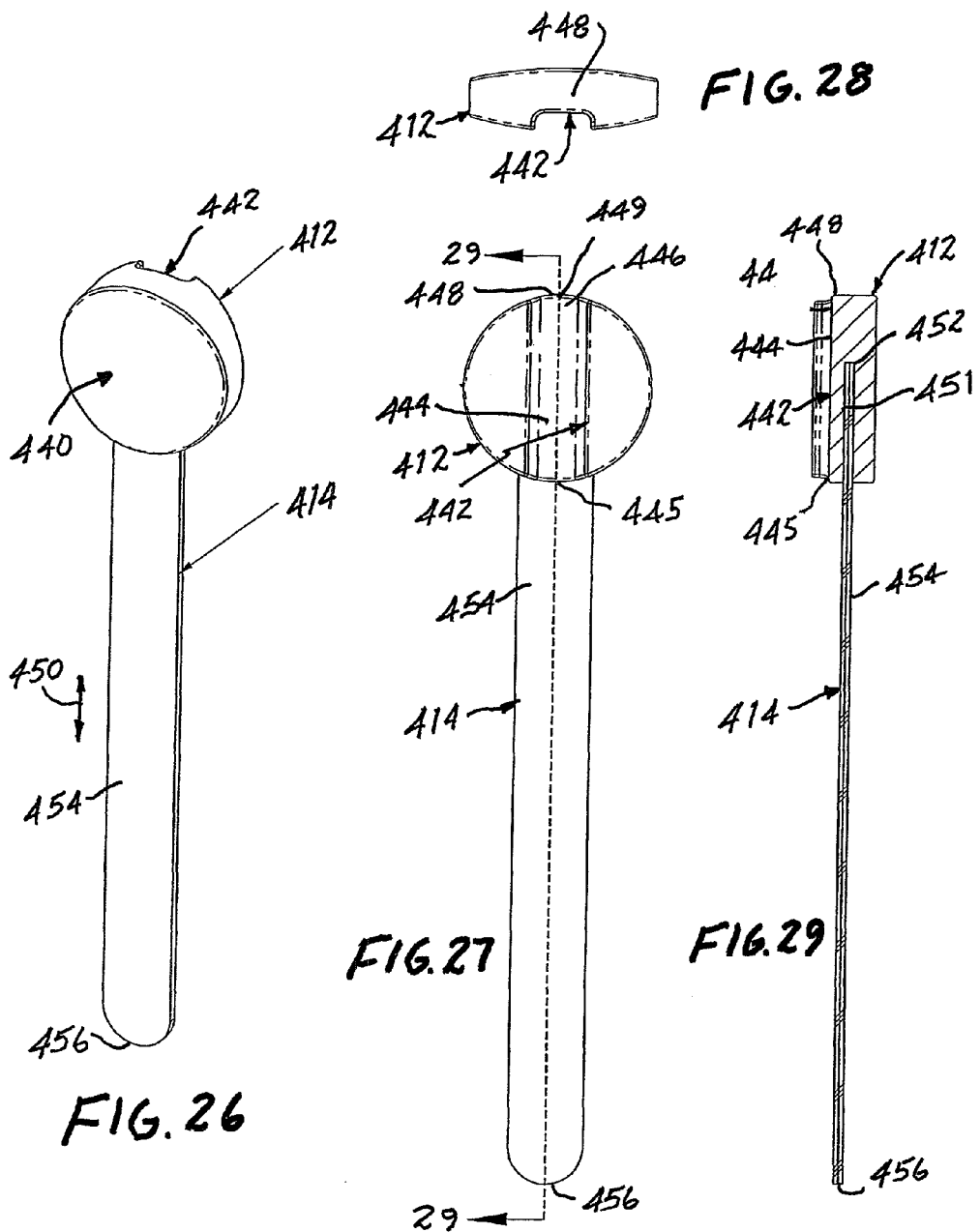

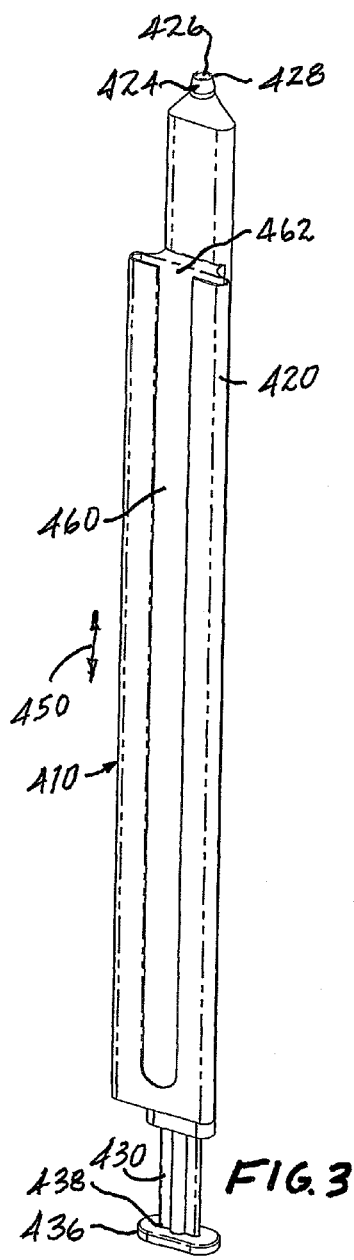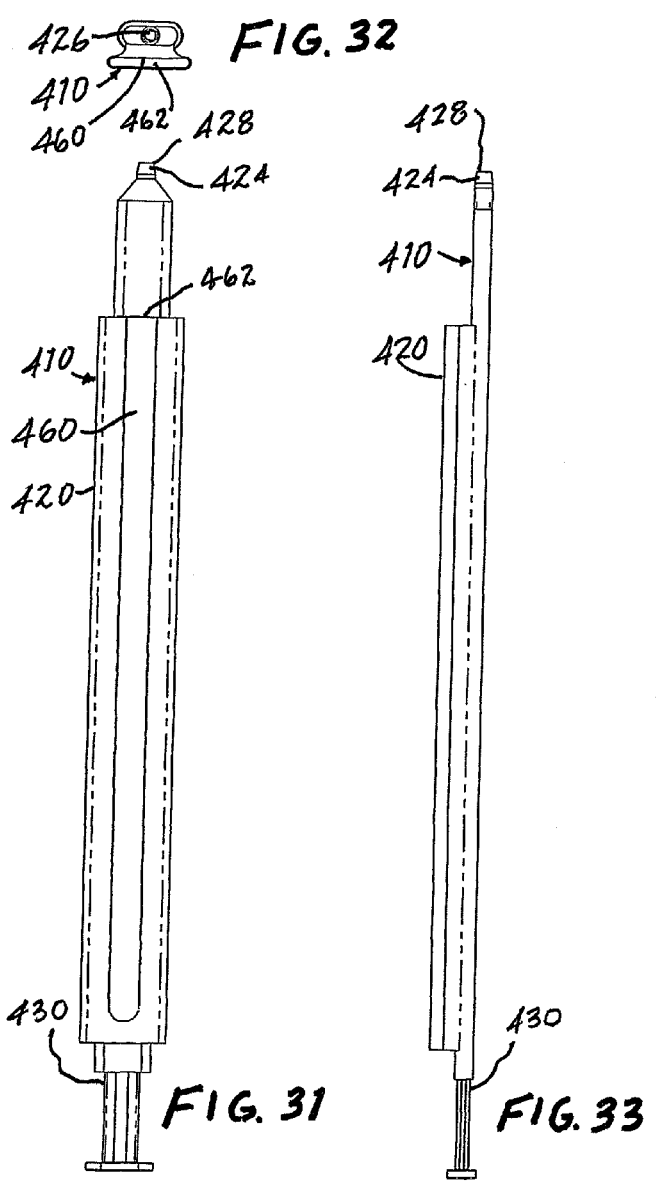

ORALLY ADMINISTERING A FLAVORED MEDICATION

This is a continuation-in-part of application Ser. No. 12/722,830, filed Mar. 12, 2010, the disclosure of which is incorporated herein by reference thereto.

The present invention relates generally to administering medication orally and pertains, more specifically, to apparatus and method for orally administering to a recipient a medication and a flavor for rendering the medication more palatable to the recipient.

The oral administration of medication often meets with resistance from a recipient because of the basically unpalatable taste of the medication. Especially where a medication such as, for example, a liquid antibiotic is to be administered orally to a child, it becomes difficult, if not impossible, to do so quickly and with the assurance that a requisite dosage has, in fact, been administered. Parents often are faced with using a spoon, an oral syringe or an oral dropper to feed a medication to a child who will resist admitting the medication, let alone swallowing a full dose, because of the unpleasant taste of the medication. The end result is a messy and unpleasant experience for both the child and the parents, and uncertainty concerning whether or not the child has received the required amount of medication. Even doctors or nurses who must administer a prescribed dose of medication to a child, either in a hospital setting or in a pediatrician's office, are met with such resistance as to reduce to guessing about the amount of medication actually received by the child. Force feeding a child a foul tasting medication only exacerbates the problem and ends in a bad experience for all involved and, most of all, for the child.

In order to alleviate the problem, medications have been flavored to render them more palatable. Usually, a selected flavor is added to a medication upon order, since it is not feasible to stock already flavored medications, due to the wide variety of flavors available, as well as to the necessity for maintaining accuracy in measuring a requisite dose of medication. In most instances, parents will have a pharmacist prepare a prescribed medication with a suitable flavor by adding a selected flavor to the medication upon order, accepting the added time and expense in favor of convenience and reduced resistance from the patient. Thus, while the flavoring of a medication for oral administration, and especially for administration to a child, has been shown to be effective, there is a need for a system that enables the oral administration of a flavored medication with greater convenience, ease and economy.

The present invention enables the oral administration of a flavored medication, and especially to a child, in a manner which avoids the problems outlined above. As such, the present invention attains several objects and advantages, some of which are summarized as follows: Provides apparatus and method for orally administering a medication and flavoring quickly and easily; assures that the recipient of a flavored oral medication receives an accurate measure of medication so as to make certain that a prescribed dose actually has been administered; avoids conflicts between patients and persons administering oral medication, and especially between children and parents, and concomitant bad experiences otherwise associated with taking an oral medication; provides increased safety, both from the standpoint of physical injury as well as the administration of a precisely measured dose of oral medication; enables increased economy as well as convenience in providing a readily-administered flavored oral medication; establishes an essentially pleasant experience which will encourage a child to accept the oral administration of a medication with a certain amount of enjoyment; avoids the use of potentially inaccurate and messy implements in the administration of an oral medication by providing a simple and effective apparatus; provides an apparatus for administering an oral medication, capable of exemplary performance over an extended service life.

The above objects and advantages, as well as further objects and advantages, are attained by the present invention which may be described briefly as apparatus for orally administering to a recipient a medication, in a liquid form, and a flavor for rendering the medication more palatable to the recipient, the apparatus comprising: a manual pressure-operated liquid dispenser for containing a measured dose of the medication, the dispenser including a dispensing outlet; an administering head for placement within a recipient's mouth, the administering head comprising an edible flavored material; a handle affixed to the administering head, the handle projecting from the administering head for enabling grasping to hold the administering head in place within the recipient's mouth during administering of the measured dose of medication; and a coupling arrangement for selective coupling of the manual pressure-operated liquid dispenser with the handle, with the dispensing outlet placed in juxtaposition with the administering head; the manual pressure-operated liquid dispenser being arranged for selective operation to advance the medication through the dispensing outlet to administer the measured dose of medication to the recipient's mouth while flavor is derived from the edible flavored material for being present with the measured dose of medication.

In addition, the present invention provides a method for orally administering to a recipient a medication, in a liquid form, and a flavor for rendering the medication more palatable to the recipient, the method comprising: providing a manual pressure-operated liquid dispenser for containing a measured dose of the medication, the dispenser including a dispensing outlet; providing an administering head with an edible flavored material for placement within a recipient's mouth, the administering head comprising an edible flavored material; providing a handle affixed to the administering head with the handle projecting from the administering head; coupling the manual pressure-operated liquid dispenser with the handle, with the dispensing outlet placed in juxtaposition with the administering head; and manually operating the pressure-operated liquid dispenser to advance the medication through the dispensing outlet, while holding the administering head in place within the recipient's mouth, to administer the measured dose of medication to the recipient's mouth while flavor is derived from the edible flavored material for being present with the measured dose of medication.

Further, the present invention includes a liquefying device for use in an apparatus for orally administering to a recipient a medication and a flavor, in a liquid form, for rendering the medication more palatable to the recipient, the liquefying device comprising: a receptacle for receiving a medication in a non-liquid form to be dispersed within the flavor, the receptacle having a manually collapsible wall; a base for carrying the receptacle while the wall is in a first configuration for receiving medication in a non-liquid form; a closure for closing the receptacle to contain the medication within the wall of the receptacle while the receptacle is moved manually into a second configuration wherein the receptacle is kneaded manually to crush the non-liquid medication; and a coupling arrangement for coupling a dispenser with the receptacle to transfer the medication into the dispenser.

The invention will be understood more fully, while still further objects and advantages will become apparent, in the following detailed description of preferred embodiments of the invention illustrated in the accompanying drawing, in which:

FIG. 13 is an exploded pictorial view of another apparatus constructed in accordance with the present invention;

FIG. 14 is a front, left side pictorial view of the apparatus of FIG. 13;

FIG. 15 is an enlarged fragmentary view of a portion of FIG. 14 indicated by arrow 15 in FIG. 14;

FIG. 16 is a side elevational view of the apparatus;

FIG. 17 is a longitudinal cross-sectional view taken along line 17-17 of FIG. 16;

FIG. 18 is an enlarged fragmentary view of a portion of FIG. 17 indicated by arrow 18 in FIG. 17;

FIG. 19 is an enlarged fragmentary view of a portion of FIG. 17 indicated by arrow 19 in FIG. 17;

FIG. 20 is an exploded pictorial view of another apparatus constructed in accordance with the present invention;

FIG. 21 is a front, right side pictorial view of the apparatus of FIG. 20;

FIG. 22 is a rear, right side pictorial view of the apparatus;

FIG. 23 is a rear elevational view of the apparatus;

FIG. 24 is a top plan view of the apparatus;

FIG. 25 is a longitudinal cross-sectional view taken along line 25-25 of FIG. 23;

FIG. 26 is a front, right side pictorial view of a component part of the apparatus;

FIG. 27 is a front elevational view of the component part of FIG. 26;

FIG. 28 is a top plan view of the component part;

FIG. 29 is a longitudinal cross-sectional view taken along line 29-29 of FIG. 27;

FIG. 30 is a front, right side pictorial view of another component part of the apparatus;

FIG. 31 is a front elevational view of the component part of FIG. 30;

FIG. 32 is a top plan view of the component part; and

FIG. 33 is a right side elevational view of the component part.

Figure 1:
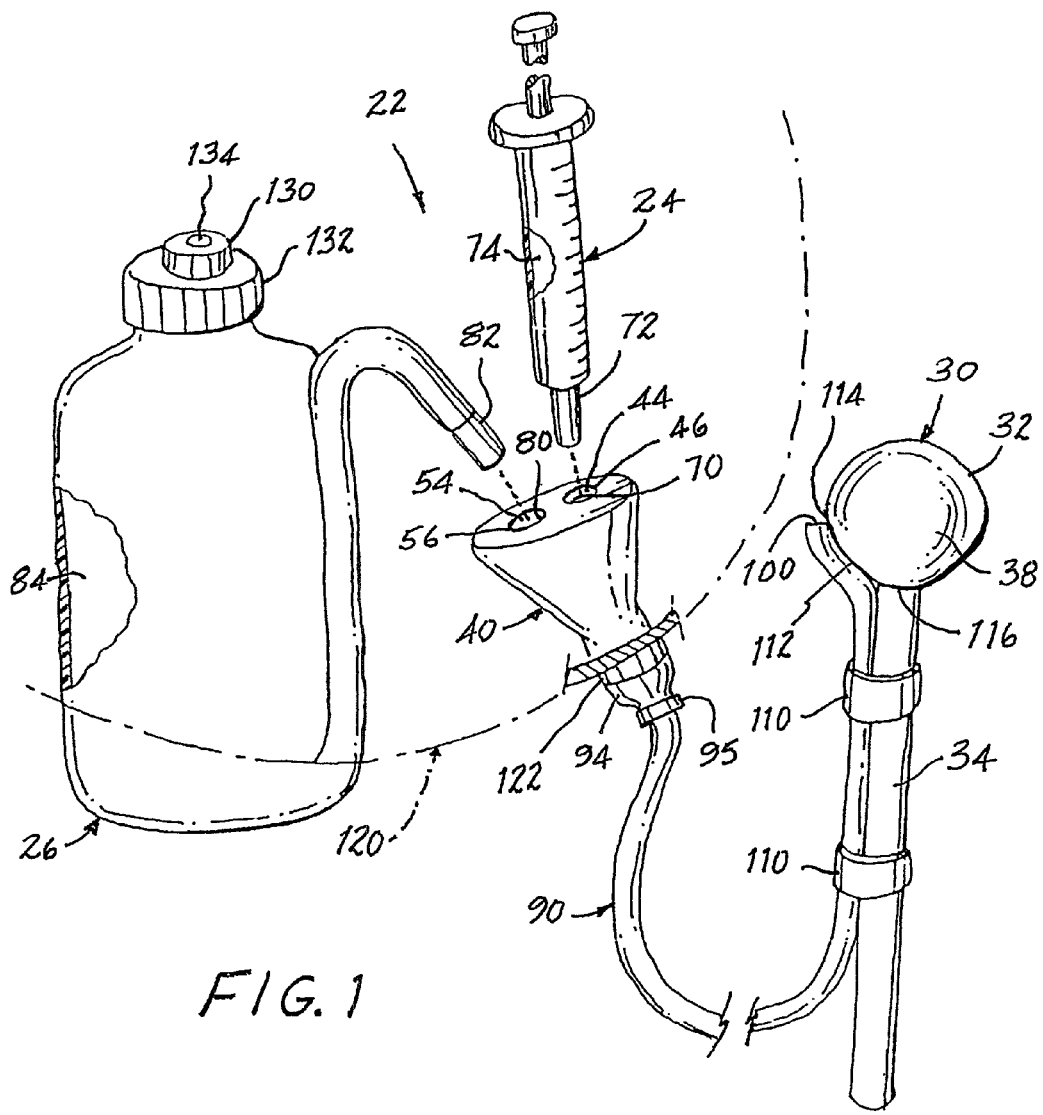
FIG. 1 is a partially diagrammatic, exploded pictorial view of an apparatus constructed in accordance with the present invention.
Figure 2:
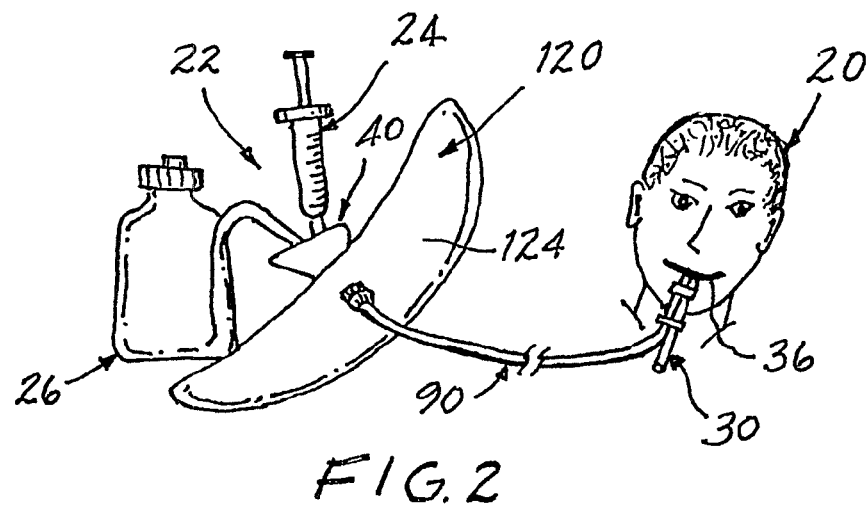
FIG. 2 is a pictorial view, reduced in size, of the apparatus, configured for, and during the oral administration of a flavored medication.

Referring now to the drawing, and especially to FIGS. 1 and 2 thereof, apparatus for orally administering a medication and a flavor for rendering the medication more palatable to a recipient 20 is shown at 22 and is seen to include a first manual pressure-operated liquid dispenser in the form of a syringe 24 for containing the medication, such as an antibiotic in liquid form, and a second manual pressure-operated liquid dispenser in the form of a squeeze bottle 26 for containing a flavor, such as a pleasant tasting fruit juice, namely, apple juice, grape juice or the like, or any one of a number of commercially available flavors currently offered for the flavoring of medications.

An administration device is shown in the form of a lollipop-like implement 30 which provides an administering head in the form of head 32, and a handle 34 projecting from the head 32 for enabling grasping, either by the recipient 20 of the medication or by a person (not shown) administering the medication. In the preferred embodiment, head 32 is constructed of an edible material, such as a candy product, which encourages the recipient 20 to admit the head 32 into the recipient's mouth 36, as seen in FIG. 2, and to maintain the head 32 in the mouth 36 during administration of the medication, as will be described below. Head 32 includes an external surface 38 configured for placement in the mouth 36 with convenience and ease, and for retention in the mouth 38 with comfort and safety, the preferred configuration being spherical, as shown.

Figure 3:
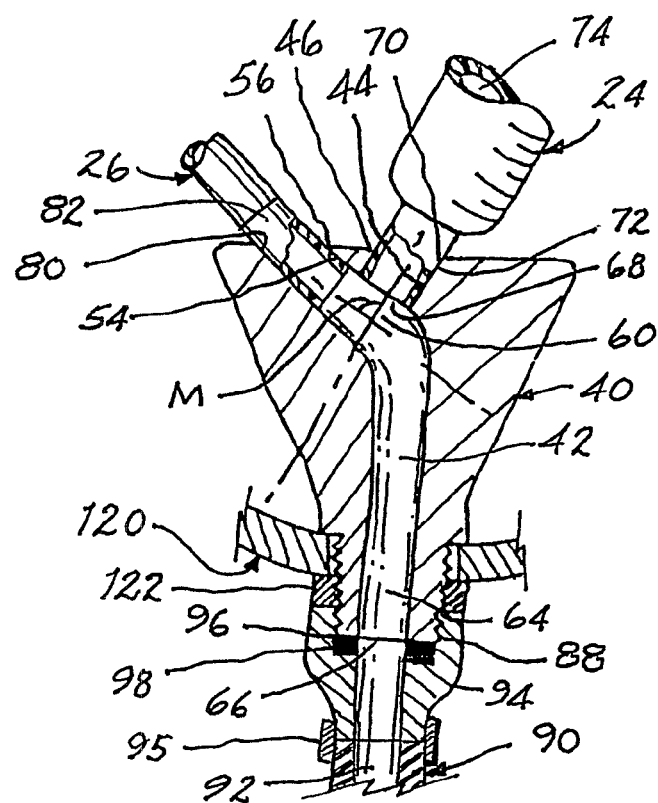
FIG. 3 is an enlarged, fragmentary longitudinal cross-sectional view of a portion of the apparatus.

Turning now to FIG. 3, as well as with reference to FIGS. 1 and 2, a manifold 40 includes a conduit 42 having a first passage 44 communicating with a corresponding first inlet 46 and a second passage 54 communicating with a corresponding second inlet 56. The passages 44 and 54 merge at a merging location 60, wherein the passages 44 and 54 merge at a merging angle M, to communicate with a third passage 64 leading to a corresponding outlet 66. A coupling arrangement couples the syringe 24 and the squeeze bottle 26 with the manifold 40 to enable the contents of the syringe 24 to be introduced into first passage 44, through an egress opening 68, and the contents of the squeeze bottle 26 to be introduced into second passage 54. To that end, first passage 44 includes a receptacle 70 at inlet 46 for receiving a tubular projection 72 of the syringe 24 in a retention fit that couples the syringe 24 with the manifold 40 and establishes communication between the interior 74 of syringe 24 and the merging location 60, with the egress opening 68 placed in close proximity with the merging location 60. In a like construction, second passage 54 includes a receptacle 80 at inlet 56 for receiving a nozzle-like projection 82 of the squeeze bottle 26 in a retention fit that establishes communication between the interior 84 of squeeze bottle 26 and the merging location 60. Manifold 40 includes a threaded nipple 88 adjacent outlet 66 of passage 64, and a flexible tube 90 having an internal passage 92 is coupled with nipple 88, by means of a threaded collar 94 affixed to tube 90 by a sleeve 95 and threaded onto threaded nipple 88. Upon securing tube 90 to manifold 40, internal passage 92 is joined with third passage 64, with the joint 96 between outlet 66 and internal passage 92 sealed by a washer 98 such that the conduit established by passages 44, 54 and 64 is continued by passage 92 through tube 90 to a common outlet 100.

Flexible tube 90 is extended to implement 30 and is affixed to handle 34 by means of securing members shown in the form of clips 110 which are selectively engaged with the handle 34 to secure tube 90 to handle 34, as shown in FIGS. 1 and 2. In the illustrated preferred arrangement, tube 90 is extended along a side area 112 of external surface 38 of head 32, following the contour configuration of the external surface 38 to locate the common outlet 100 at the side 114 of the head 32, the handle 34 projecting from an end area 116 of the surface 38. In this manner, implement 30 can be chosen from a variety of standard commercially available lollipops, if desired. With the tube 90 affixed to handle 34, as shown, a measured volume of medication placed in the interior 74 of syringe 24, and a flavor carried within the interior 84 of squeeze bottle 26, head 32 is placed within the mouth 36 of the recipient 20, thereby locating common outlet 100 toward the side of the recipients's mouth 36. In order to alleviate any apprehension a child may have upon encountering apparatus 22, a mask 120 is secured to manifold 40, as by a retainer 122 threaded onto nipple 88, and extends over the manifold 40, between the manifold 40 and the implement 30, to hide the manifold 40, the syringe 24 and the squeeze bottle 26 from the child's view. Mask 120 can be decorated, along face 124 of the mask 120, with any number of entertaining characters or scenes which can appeal to a child.

Administration of the medication then can be accomplished in any one of alternate sequences of operation of the components of apparatus 22. Thus, operating apparatus 22 to actuate syringe 24 manually to pass medication through passage 44 to merging location 60, while simultaneously manually squeezing squeeze bottle 26 to pass flavor through passage 54 to merging location 60, will result in a mixture of medication and flavor, created at the merging location 60, to be passed through outlet 66, thence through tube 90 to common outlet 100, where the mixture will enter the recipient's mouth 36, flavored so as to be accepted readily by the recipient 20. With the common outlet 100 placed adjacent the side of the recipient's mouth 36, the mixture is dispensed at a location found to be most effective in administering oral medication.

As best seen in FIG. 3, the merging angle M between the passages 44 and 54, together with the close proximity of the tubular projection 72 of syringe 24 will tend to purge passage 44 of all medication as flavor continues to flow through merging location 60. In the preferred construction, merging angle M is no more than 90°. In this manner, the flow of flavor through merging location 60 and to common outlet 100 will tend to deliver the full measure of medication to the recipient 20. However, as an alternate procedure, squeezing of the squeeze bottle 26 is continued, subsequent to completion of the actuation of syringe 24 to expel the full measured volume of medication in the dose to be administered, to assure that the full measured volume of medication is drawn from syringe 24 and carried to the recipient 20. Preferably, tube 90 is constructed of a transparent or semi-transparent material so that a visual determination is available to confirm completion of the flow of medication to the common outlet 100.

In another alternate sequence of operations, the squeeze bottle 26 is squeezed initially, prior to actuation of syringe 24, to introduce flavor to the recipient 20 prior to administering any medication, so as to encourage acceptance of a flow through tube 90 and common outlet 100 and enable a concomitant smooth transition as medication subsequently is introduced into the stream of flavor by the subsequent actuation of syringe 24. Here again, the flow of flavor from squeeze bottle 26 can be continued until all medication is purged from the conduit established by passages 44, 54, 64 and 92, and is delivered to the recipient 20.

The provision of a squeeze bottle 26 having a relatively large capacity, well in excess of any measured volume of medication placed in syringe 24, facilitates any of the sequences of operation set forth above. Moreover, the large volume of squeeze bottle 26 enables the convenient storage of flavor for multiple sessions of oral administration of medication, with concomitant economy. In order to preclude any contamination of the flavor stored in squeeze bottle 26 by medication which might be drawn back into squeeze bottle 26 at the conclusion of a session of oral administration, a vent 130 is placed in cap 132 of squeeze bottle 26, and a check valve 134 within vent 130 assures that upon squeezing of squeeze bottle 26, vent 130 will be closed and flavor will be driven through projection 82 to passage 54 of manifold 40. However, upon release of the squeeze which drives flavor from the squeeze bottle 26 to manifold 40, check valve 134 will open to enable ambient air to pass into the interior of squeeze bottle 26, thereby precluding any flow back from manifold 40 into squeeze bottle 26.

Tube 90 is detached readily from handle 34 of implement 30 merely by opening clips 110, and is detached selectively from manifold 40 by releasing collar 94 from nipple 88. In this manner, tube 90, as well as manifold 40, can be cleaned easily for subsequent reuse. However, tube 90 is quite inexpensive and therefore readily expendable, and can be replaced economically for each use, thereby maintaining sanitary conditions and promoting safety.

Figure 5:
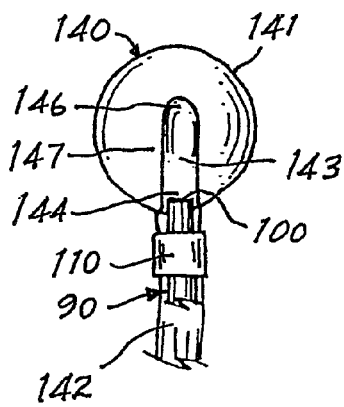
FIG. 5 is a fragmentary side elevational view of the embodiment of FIG. 4.
Figure 4:
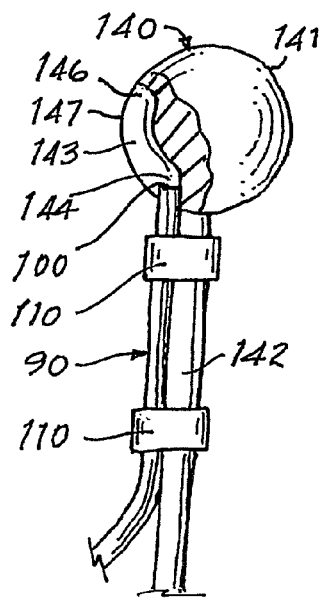
FIG. 4 is a front elevational view, partially sectioned, showing an alternate embodiment of a component part of the apparatus.

Referring now to FIGS. 4 and 5, an alternate implement 140 is constructed similar to implement 30 in that implement 140 includes a head 141 and a handle 142 projecting from the head 141 in a lollipop-like configuration. As before, tube 90 is affixed to handle 142 by clips 110 to place common outlet 100 in juxtaposition with head 141. However, in order to facilitate the conduct of liquid from tube 90 to the side of a recipient's mouth, a channel 143 is provided in head 141 and is configured along an arcuate shape to direct medication and flavor from an entrance 144, juxtaposed with the common outlet 100, to emanate along the length of channel 143, as well as from an exit 146 at a side area 147 of the head 141.

Figure 6:
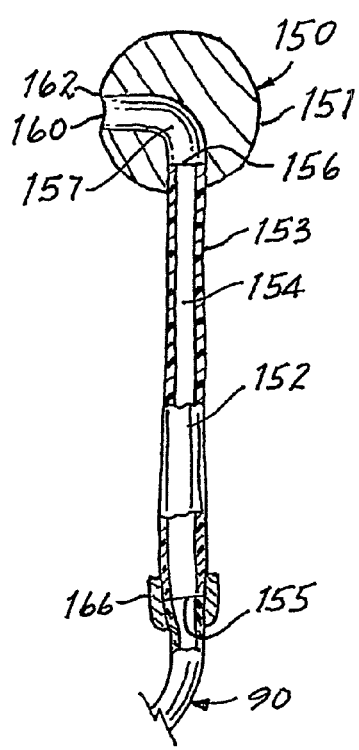
FIG. 6 is a front elevational view, shown largely in cross-section, showing another embodiment of a component part of the apparatus.

In another alternate embodiment, illustrated in FIG. 6, implement 30 is replaced by implement 150, also having an overall lollipop-like configuration. A head 151 has a generally spherical configuration, as do heads 32 and 141, and a handle 152 projects from head 151. In the present embodiment, however, handle 152 is in the form of a shaft 153 having an internal duct 154 which extends upwardly from a first duct end 155 to a second duct end 156. An internal passage 157 extends into head 151 and is directed from an ingress port 159 to an egress port 160 placed at the side 162 of head 151. Tube 90, then, is coupled with handle 152 at the first duct end 155, as by a coupling 166. Medication and flavor are passed through duct 154 in handle 152 to head 151 to pass through internal passage 157 and emanate from head 151 at egress port 160.

Figure 8:
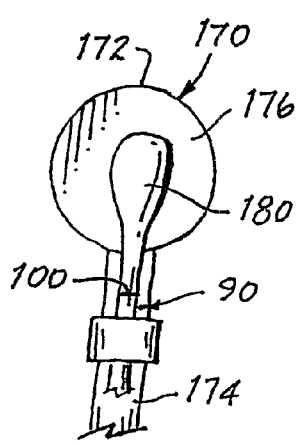
FIG. 8 is a fragmentary side elevational view of the embodiment of FIG. 7.
Figure 7:
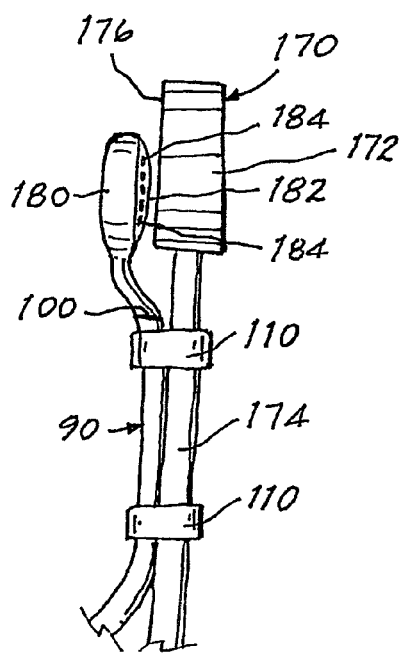
FIG. 7 is a front elevational view showing still another embodiment of a component part of the invention.

An alternate embodiment is illustrated in FIGS. 7 and 8 in the form of implement 170 having a head 172 and a handle 174 projecting from the head 172 to establish a lollipop-like configuration. In this instance, head 172 has a disk-like configuration with a side face 176. As before, tube 90 is secured to handle 174 with clips 110. A distributor 180 is affixed to tube 90, at common outlet 100, and has a distributor face 182 placed so as to confront side face 176 of head 172. Distributor face 182 is provided with a plurality of apertures 184 so that medication and flavor supplied through tube 90 to distributor 180 is disbursed along side face 176 for delivery to a recipient.

Figure 9:
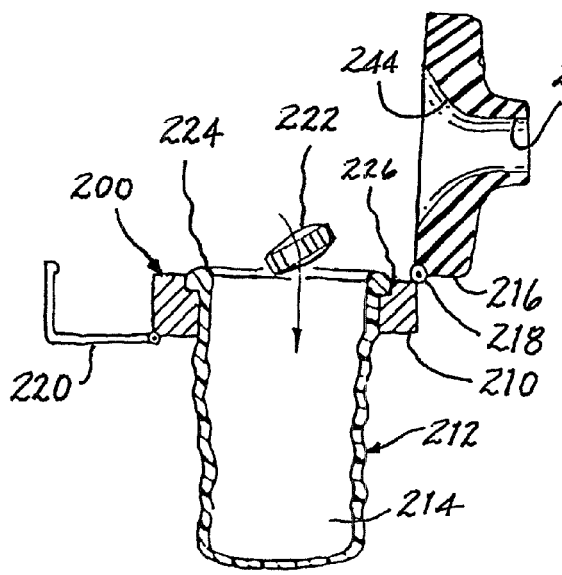
FIGS. 9 through 12 are longitudinal cross-sectional views of another component part of the apparatus showing consecutive stages in the operation of the component part of the apparatus.
Figure 10:
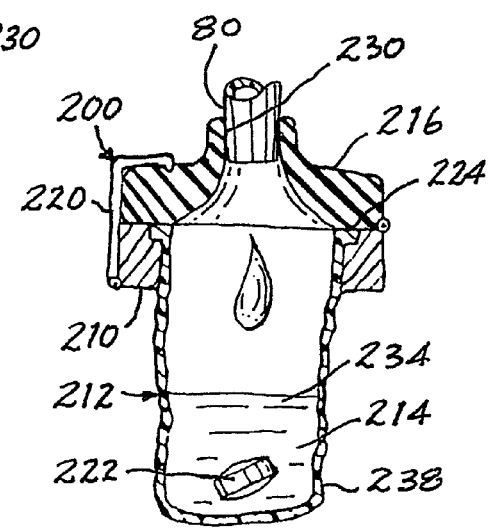

Turning now to FIGS. 9 through 12, in order to accommodate medication furnished in a form other than a liquid form, as described above, that is, a non-liquid medication which may be supplied in the form of a tablet, or in a powdered form, perhaps derived from a capsule, apparatus 30 is provided with a liquefying device 200 for facilitating the charging of syringe 24 with a volume of liquid containing a prescribed dose of medication. Liquefying device 200 includes a base 210 within which there is mounted a bag-like receptacle 212 proving a reservoir 214. A cover 216 is hinged to the base 210 by means of a hinge 218, and a latch 220 is mounted upon the base 210 for pivotal movement, as will now be described. In the preferred construction, cover 216 is constructed of a resilient elastomeric material. With the liquefying device 200 in an open configuration, as shown in FIG. 9, medication, here shown in the non-liquid form of a tablet 222, is placed in receptacle 212. Once the tablet 222 is placed within reservoir 214, cover 216 is moved into the closed position illustrated in FIG. 10, and is latched closed by means of latch 220. At the same time, a bead 224 around the perimeter 226 of receptacle 212 seals the reservoir 214 against leakage along the perimeter 226.

Figure 11:
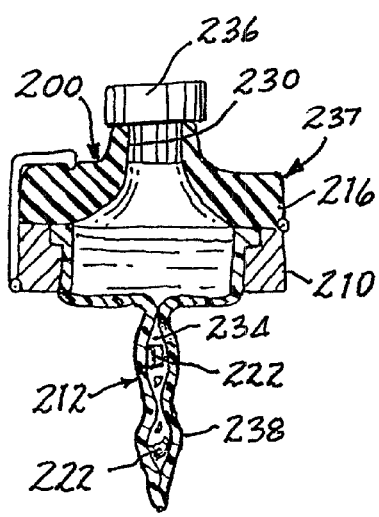

Then, projection 82 of squeeze bottle 26 is engaged with a cylindrical seat 230 extending through the cover 216, the resilient characteristics of the material of cover 216 establishing a sealed connection between projection 82 and seat 230. Once the projection 82 is fully seated, a liquid flavor 234 is introduced into reservoir 214 by squeezing the squeeze bottle 26. With a volume of flavor 234 in reservoir 214, a plug 236 is seated and secured in place within seat 230, as seen in FIG. 11, and seat 230 is sealed so that, together with cover 216, a closure 237 is completed which closes receptacle 212. Receptacle 212 has a highly flexible wall 238 and, with the tablet 222 and flavor 234 in the reservoir 214, wall 238 is collapsed and receptacle 212 is kneaded, as illustrated in FIG. 11, to crush the tablet 222 and dissolve, or at least disperse, the medication in the liquid flavor 234. In an alternate procedure, tablet 222 can be inserted into receptacle 212 and crushed prior to placement of flavor 234 into reservoir 214, with flavor 234 then being added into reservoir 214 subsequent to crushing of tablet 222. Such a procedure facilitates the crushing and dispersion of a harder, more dense tablet 222.

Figure 12:
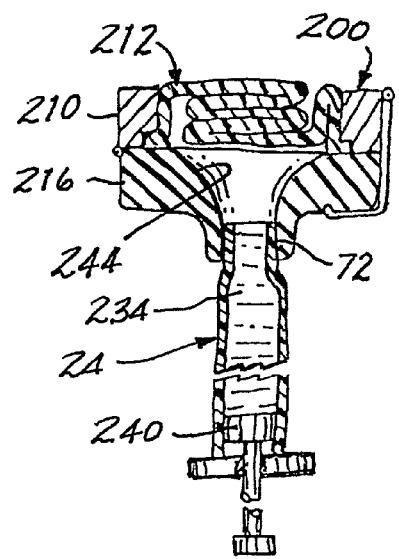

Once the medication is fully dissolved or dispersed, syringe 24 is coupled with liquefying device 200 by seating tubular projection 72 within the cylindrical seat 230, as seen FIG. 12. With syringe 24 fully coupled with liquefying device 200, and with reservoir 214 containing the flavor 234 with the dissolved or dispersed medication, the coupled liquefying device 200 and syringe 24 are inverted, and plunger 240 of syringe 24 is retracted, as illustrated in FIG. 12, such that the contents of reservoir 214 of receptacle 212 flow into syringe 24, assisted by gravity and by a funnel-like configuration along interior surface 244 of cover 216, thereby effectively charging syringe 24 with a volume of flavor 234 containing the prescribed dose of medication. Subsequently, receptacle 212, which is inexpensive and therefore expendable, merely is removed from base 210 and is discarded, to be replaced by a fresh receptacle 212, thereby avoiding any deleterious consequences which could be associated with reusing a previously-used receptacle 212 upon subsequently charging a syringe 24 for another session of administering an oral medication.

While in the illustrated preferred embodiments, manifold 40 is shown with a construction which accommodates one syringe 24, and one squeeze bottle 26, it will be apparent that manifold 40 can be replaced with a similar manifold in which multiple passages can accommodate either multiple syringes for the administration of multiple medications during a single session of administering oral medication, or multiple squeeze bottles for dispensing multiple flavors, or multiple syringes and multiple squeeze bottles providing a high degree of flexibility when administering flavored oral medication.

Referring now to FIGS. 13 through 19, another apparatus constructed in accordance with the present invention is shown at 300 and is seen to include a manual pressure-operated liquid dispenser in the form of a syringe 310 for containing a measured dose of medication to be administered, an administering head 312 for placement within a recipient's mouth, in a manner similar to that described above in connection with the embodiments illustrated in FIGS. 1 through 7, and a handle 314 affixed to the administering head 312 for enabling grasping to hold the administering head 312 in place within the recipient's mouth during administration of the measured dose of medication.

Syringe 310 has a cylindrical body 320 with an internal chamber 322 for containing the measured dose of medication, and a dispensing tip 324 presents a dispensing outlet 326 at one end 328 of the body 320, through which dispensing outlet 326 the medication is delivered by movement of a plunger 330 within the chamber 322, as is conventional in the construction of syringes. Movement of the plunger 330 is facilitated by providing a finger grip 332 at the other end 334 of the body 320, and a thumb pad 336 at the end 338 of plunger 330.

Administering head 312 is comprised of an edible, flavored material, such as a candy product, and is shown in a generally spherical configuration. Administering head 312 includes an external surface 340 which, in this instance, is generally spherical, and a passage in the form of an internal passage 342 extends diametrically through the administering head 312, providing a socket portion 344 and a duct 345 communicating with an egress in the form of egress port 346 at a surface portion 348 of the administering head 312 that will be certain to be located within the recipient's mouth upon placing the administering head 312 within the recipient's mouth. Thus, while the administering head 312 is shown in the generally spherical configuration, administering head 312 can be constructed in any one of a variety of shapes amenable to the reception of at least a portion of the administering head 312 within a recipient's mouth, which portion will place an egress port, such as egress port 346, within the recipient's mouth. However, the generally spherical configuration of administering head 312 resembles a now well-known lollipop configuration, rendering the administering head 312 simple and economical to manufacture, while being readily recognized by a recipient as an item that provides a pleasing taste, thereby attaining ready acceptance by the recipient and facilitating administering of the medication. Further, the spherical configuration provides the administering head 312 with a volume that is very large in comparison with the volume of any measured dose of medication so that flavor is available throughout the administering of the measured dose of medication.

Handle 314 extends along an axial direction 350 and includes a tubular member 352 received, adjacent a first end 353 of tubular member 352, within socket portion 344 of passage 342 in administering head 312 to affix handle 314 to administering head 312, as seen in FIGS. 17 and 18, while providing a convenient hand grip at 354.

Upon preparing for use of apparatus 300, syringe 310 is first charged with a desired measured dose of medication, while syringe 310 is outside of tubular member 352 of handle 314, as seen in FIG. 13. Once so charged, syringe 310 is coupled with handle 314, to join the syringe 310 with handle 314, by inserting the syringe 310 into a receptacle in the tubular member 352 of handle 314, the receptacle being in the form of a circular cylindrical inner bore 356 that extends axially along the handle 314 from an opening 358 at end 359 of tubular member 352, and is complementary to the external configuration of the body 320 of syringe 310. In this manner, syringe 310 is inserted through opening 358 to be fitted within inner bore 356 and extends axially along inner bore 356 until fully seated within inner bore 356, with dispensing tip 324 juxtaposed with surface portion 348 of administering head 312 and presenting dispensing outlet 326 at egress port 346, as seen in FIGS. 17 and 18. A securing mechanism is provided for retaining syringe 310 joined with handle 314 and is shown in the form of a flange 360 integral with handle 314 and extending radially outwardly from tubular member 352. With syringe 310 seated in place within handle 314, a clip 362, integral with body 320 of syringe 310 and projecting outwardly from body 320, is snapped over flange 360, as seen in FIGS. 17 and 19, as well as in FIG. 14, to secure syringe 310 in place within handle 314. Clip 362 is selectively released readily from flange 360 when it is desired to remove syringe 310 from engagement with handle 314.

With syringe 310 charged and secured within handle 314, as seen in FIG. 14, administering head 312 is placed within a recipient's mouth, and syringe 310 is actuated to move plunger 330 forward and dispense the measured dose of medication. The medication is advanced through dispensing outlet 326 and egress port 346 to pass into the recipient's mouth. The close proximity of dispensing outlet 326 to egress port 346, and surface portion 348 of administering head 312, assures that substantially the entire measured dose of medication is dispensed into the recipient's mouth, while flavor is derived from the edible flavored material of the administering head 312 for being present with the measured dose of medication.

Referring now to FIGS. 20 through 33, another apparatus constructed in accordance with the present invention is shown at 400 and is seen to include a manual pressure-operated liquid dispenser in the form of a syringe 410 for containing a measured dose of medication to be administered, an administering head 412 for placement within a recipient's mouth, in a manner similar to that described above in connection with the embodiment illustrated in FIGS. 13 through 19, and a handle 414 affixed to the administering head 412 for enabling the administering head 412 to be joined with syringe 410 and held in place within the recipient's mouth during administration of the measured dose of medication.

Syringe 410 has a body 420 with an internal chamber 422 (see FIG. 25) for containing the measured dose of medication, and a dispensing tip 424 presents a dispensing outlet 426 (see FIGS. 24, 30 and 32) at one end 428 of the body 420, through which dispensing outlet 426 the medication is delivered by movement of a plunger 430 within the chamber 422, as is conventional in the construction of syringes. Movement of the plunger 430 is facilitated by providing a thumb pad 436 at end 438 of plunger 430.

Administering head 412 is comprised of an edible, flavored material, such as a candy product, and is shown in a generally disk-like cylindrical configuration. Administering head 412 includes an external surface 440 which, in this instance, has a generally cylindrical configuration. A passage in the form of a groove 442 extends diametrically across the administering head 412, providing a recess portion 444 adjacent a first end 445 of groove 442 and an egress in the form of egress area 446 at a surface portion 448 adjacent a second end 449 of groove 442 such that surface portion 448 will be certain to be located within the recipient's mouth upon placing the administering head 412 within the recipient's mouth. Thus, while the administering head 412 is shown in the generally disk-like cylindrical configuration, administering head 412 can be constructed in any one of a variety of shapes amenable to the reception of at least a portion of the administering head 412 within a recipient's mouth, which portion will place an egress, such as egress area 446, within the recipient's mouth. However, the disk-like cylindrical configuration of administering head 412 resembles a now well-known lollipop configuration, rendering the administering head 412 simple and economical to manufacture, while being readily recognized by a recipient as an item that provides a pleasing taste, thereby attaining ready acceptance by the recipient and facilitating administering of the medication. Further, the disk-like cylindrical configuration provides the administering head 412 with a volume that is very large in comparison with the volume of any measured dose of medication so that flavor is available throughout the administering of the measured dose of medication.

Handle 414 extends along a longitudinal direction 450, is affixed to administering head 412, within a slot 451 in head 412, adjacent an end 452, and includes a handling section 454 projecting from administering head 412, as seen in FIG. 29. In a preferred configuration, handle 414 resembles a POPSICLE® stick, having a generally rectangular lateral cross-sectional configuration and a rounded terminal end 456 longitudinally opposite end 452.

Upon preparing for use of apparatus 400, syringe 410 is first charged with a desired measured dose of medication, while the syringe 410 is disconnected from handle 414, as seen in FIGS. 30 through 33. Once so charged, syringe 410 is connected to handle 414, to join the syringe 410 with handle 414, and with administering head 412, by inserting handling section 454 of the handle 414 into a receptacle constructed integral with, and preferably unitary with, the body 420 of syringe 410, the receptacle being in the form of a channel 460 having an entrance 462 adjacent dispensing tip 424 and extending longitudinally along the body 420 of syringe 410, the channel 460 having a generally rectangular lateral cross-sectional configuration complementary to the lateral cross-sectional configuration of the handle 414. Insertion of the handle 414 through entrance 462 and into the channel 460 is facilitated by the rounded configuration at terminal end 456 of handle 414. In this manner, handle 414 is fitted within channel 460 and extends longitudinally along channel 460 until handle 414 is fully seated within the channel 460, with dispensing tip 424 placed within recess portion 444 of groove 442 so as to be juxtaposed with egress area 446 of administering head 412 and present dispensing outlet 426 at egress area 446, as seen in FIGS. 21 through 25.

With syringe 410 charged and handle 414 fully seated within channel 460, administering head 412 is placed within a recipient's mouth, and syringe 410 is actuated to move plunger 430 forward and dispense the measured dose of medication. The medication is advanced through dispensing outlet 426 to egress area 446 to pass into the recipient's mouth. The close proximity of dispensing outlet 426 to egress area 446, and surface portion 448 of administering head 412, assures that substantially the entire measured dose of medication is dispensed into the recipient's mouth, while flavor is derived from the edible flavored material of the administering head 412 for being present with the measured dose of medication.

It will be apparent that the present invention attains all of the objectives and advantages summarized above, namely: Provides apparatus and method for orally administering a medication and flavoring quickly and easily; assures that the recipient of a flavored oral medication receives an accurate measure of medication so as to make certain that a prescribed dose actually has been administered; avoids conflicts between patients and persons administering oral medication, and especially between children and parents, and concomitant bad experiences otherwise associated with taking an oral medication; provides increased safety, both from the standpoint of physical injury as well as the administration of a precisely measured dose of oral medication; enables increased economy as well as convenience in providing a readily-administered flavored oral medication; establishes an essentially pleasant experience which will encourage a child to accept the oral administration of a medication with a certain amount of enjoyment; avoids the use of potentially inaccurate and messy implements in the administration of an oral medication by providing a simple and effective apparatus; provides an apparatus for administering an oral medication, capable of exemplary performance over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for orally administering to a recipient a medication, in a liquid form, and a flavor for rendering the medication more palatable to the recipient, the apparatus comprising:
    a manual pressure-operated liquid dispenser for containing a measured dose of the medication, the manual pressure-operated liquid dispenser including a dispensing outlet;
    an administering head for placement within a recipient's mouth, the administering head comprising an edible flavored material;
    a handle affixed to the administering head, the handle projecting from the administering head for enabling grasping to hold the administering head in place within the recipient's mouth during administering of the measured dose of medication; and
    a coupling arrangement for selective coupling of the manual pressure-operated liquid dispenser with the handle, with the dispensing outlet placed in juxtaposition with the administering head;
    the manual pressure-operated liquid dispenser being arranged for selective operation to advance the medication through the dispensing outlet to administer the measured dose of medication to the recipient's mouth while flavor is derived from the edible flavored material for being present with the measured dose of medication; and wherein
    the administering head includes an external surface having at least a surface portion located along the administering head for extending into the recipient's mouth upon placement of the administering head within the recipient's mouth, and a passage having an egress port at the surface portion;
    the manual pressure-operated liquid dispenser comprises a syringe having a capacity for containing the measured dose of medication, the syringe including a dispensing tip adjacent the dispensing outlet, a body having an internal chamber for containing the measured dose of medication, and a plunger movable within the chamber to dispense the measured dose of medication through the dispensing outlet; and
    the apparatus includes a receptacle for joining the syringe with the handle, with the dispensing tip placed within the passage, in juxtaposition with the surface portion of the external surface of the administering head, to locate the dispensing outlet at the egress port at the surface portion of the external surface of the administering head such that upon joining the syringe with the handle, and moving the plunger within the chamber, toward the dispensing tip, substantially all of the measured dose of medication will be dispensed through the egress port and into the recipient's mouth, flavored by the edible flavored material.

2. The apparatus of claim 1 wherein the edible flavored material comprises a candy product.

3. The apparatus of claim 1 wherein:
    the passage of the administrating head comprises an inner passage;
    the body of the syringe has an outer surface configuration extending in an axial direction along the body; and
    the receptacle comprises an inner bore extending in the axial direction within the handle, the inner bore communicating with the egress port of the administering head and being substantially complementary to the outer surface configuration of the body of the syringe such that upon coupling the syringe with the handle, the body of the syringe will be fitted within the inner bore, with the dispensing tip placed to locate the dispensing outlet at the egress port for effecting dispensing of substantially the entire measured dose of medication to the recipient.

4. The apparatus of claim 3 wherein the handle includes a first end affixed to the administering head diametrically opposite the surface portion and the egress port of the administering head, and a second end located axially opposite the first end, the inner bore including an opening at the second end for reception of the body of the syringe.

5. The apparatus of claim 4 wherein the outer surface configuration of the body of the syringe comprises a circular cylindrical configuration, and the inner bore has a complementary circular cylindrical configuration.

6. The apparatus of claim 4 including a securing mechanism for selectively securing the syringe within the handle, with the body of the syringe fitted within the inner bore of the handle.

7. The apparatus of claim 3 wherein:
    the handle has an outer configuration extending in a longitudinal direction along the handle; and
    the receptacle comprises a channel extending in the longitudinal direction along the body of the syringe, the channel communicating with the passage of the administering head and being substantially complementary to the outer configuration of the handle such that upon coupling the syringe with the handle, the handle will be fitted within the channel, and the dispensing tip will be placed to locate the dispensing outlet at the egress port of the passage of the administering head for effecting dispensing of substantially the entire measured dose of medication to the recipient.

8. The apparatus of claim 7 wherein the handle includes a first end affixed to the administering head diametrically opposite the surface portion, the passage of the administering head comprises a groove extending diametrically across the administering head, between the egress port of the passage and the handle, and a second end located longitudinally opposite the first end, the channel including an entrance adjacent the dispensing tip for reception of the handle.

9. The apparatus of claim 8 wherein the outer configuration of the handle includes a first rectangular lateral cross-sectional configuration, and the channel includes a second rectangular lateral cross-sectional configuration complementary to the first rectangular lateral cross-sectional configuration.

* * * * *